United States Patent [19]

Linenberg

[11] 4,128,008

[45] Dec. 5, 1978

[54] CONCENTRATION VALVE FOR A GAS DETECTING APPARATUS, OR THE LIKE

[75] Inventor: Amos Linenberg, North Hollywood, Calif.

[73] Assignee: Xonics, Inc., Van Nuys, Calif.

[21] Appl. No.: 793,608

[22] Filed: May 4, 1977

[51] Int. Cl.² ............................................. G01N 1/22
[52] U.S. Cl. ................................................ 73/422 GC
[58] Field of Search ........................ 73/422 GC, 23.1

[56] References Cited
U.S. PATENT DOCUMENTS

| | | | |
|---|---|---|---|
| 3,160,015 | 12/1964 | Charlton et al. | 73/422 GC |
| 3,345,858 | 10/1967 | Fenske | 73/23.1 |
| 3,362,228 | 1/1968 | Stüben | 73/422 GC |
| 3,675,466 | 7/1972 | Linenberg | 73/422 GC X |
| 3,681,996 | 8/1972 | Crist | 73/422 GC |
| 3,733,908 | 5/1973 | Linenberg | 73/422 GC |
| 3,933,165 | 1/1976 | Budzak et al. | 73/422 GC X |

Primary Examiner—Richard C. Queisser
Assistant Examiner—Joseph W. Roskos
Attorney, Agent, or Firm—Harris, Kern, Wallen & Tinsley

[57] ABSTRACT

A concentration valve for a gas detecting apparatus including a cylinder having diametrally opposed inlet and outlet ports for a sample gas and having diametrally opposed inlet and outlet ports for a carrier gas longitudinally spaced from and in the same longitudinal plane as the sample-gas inlet and outlet ports, a cylindrical plug having a diametral passage therethrough and movable longitudinally of the cylinder between a sampling position wherein the diametral passage communicates with the sample-gas inlet and outlet ports and an analyzing position wherein the diametral passage communicates with the carrier-gas inlet and outlet ports, a pneumatic actuator for longitudinally moving the cylindrical plug between the sampling and analyzing positions, gas adsorbing means in the diametral passage for adsorbing a gaseous material or materials from the sample gas, and means for heating the gas adsorbing means in the analyzing position of the cylindrical plug to desorb the previously adsorbed gaseous material or materials into the carrier gas for transfer to a gas chromatograph, or other analyzing means. The pneumatic actuating means comprises a piston to which the cylindrical plug is secured by a readily releasable connecting means so that it can be removed for replacement by one capable of adsorbing a different material.

3 Claims, 2 Drawing Figures

CONCENTRATION VALVE FOR A GAS DETECTING APPARATUS, OR THE LIKE

BACKGROUND OF INVENTION

The present invention relates to a concetration valve for a gas detecting apparatus, or the like, in a system for determining the presence a particular gaseous material or materials in a sample gas, such as air.

More specifically, the invention contemplates a concentration valve having adsorbing means operable to adsorb at least one gaseous material or vapor from a sample gas in a sampling position, and having means operable in an analyzing position for heating the adsorbing means to desorb into a carrier gas any gaseous material or vapor adsorbed from the sample gas. The carrier gas with the desorbed gaseous material or vapor therein is delivered to a suitable analyzing apparatus, e.g., a gas chromatograph.

As general background relating to the detection of a particular gaseous material or vapor from a sample gas, attention is directed to Dravnieks et al U.S. Pat. No. 3,430,482. Prior art specifically disclosing earlier concentration valves for use with apparatuses for detecting gaseous or vaporous materials in sample gases includes my U.S. Pat. Nos. 3,675,466 and 3,733,908, and Showalter et al U.S. Pat. No. 3,925,022. These patents also provide general background information respecting the field of detecting gaseous materials or vapors in sample gases, such as air. Consequently, a further discussion of the general field herein is unnecessary.

OBJECTS AND SUMMARY OF INVENTION

The primary object of the present invention is to provide a concentration valve which is of simple construction and which is capable of shifting an adsorbing means between a sampling, adsorbing position and a desorbing, analyzing position positively and quickly.

An important object of the invention is to provide a concentration valve which includes, and the invention may be summarized as comprising a concentration valve which includes, a cylinder having diametrally opposed inlet and outlet ports for a sample gas and having diametrally opposed inlet and outlet ports for a carrier gas longitudinally spaced from and in the same plane as the sample-gas inlet and outlet ports, a cylindrical plug having a diametral passage therethrough and movable longitudinally of the cylinder between a sampling position wherein the diametral passage communicates with the sample-gas inlet and outlet ports and an analyzing position wherein the diametral passage communicates with the carrier-gas inlet and outlet ports, actuating means for longitudinally moving the cylindrical plug between the sampling and analyzing positions, adsorbing means in the diametral passage and operable to adsorb a gaseous material or vapor in the sampling position, and means for heating the adsorbing means in the analyzing position to desorb the adsorbed gaseous material or vapor into the carrier gas for delivery to an analyzing apparatus, such as a gas chromatograph.

Another important object is to provide an actuating means which is pneumatic and which comprises a second cylinder coaxial with the cylinder for the cylindrical plug, a piston in the second cylinder, means for securing the cylindrical plug to the piston, and valve means for selectively directing air under pressure to opposite ends of the piston to selectively place the cylindrical plug in its sampling and analyzing positions.

Yet another significant object is to provide a construction wherein the means for securing the cylindrical plug to the piston comprises a readily releasable connecting means so that the cylindrical plug can be detached readily for replacement by one carrying a different adsorbing means for a different gaseous material or materials.

The foregoing objects, advantages, features and results of the invention, together with various other objects, advantages, features and results of the invention which will be evident to those skilled in the relevant art, may be achieved with the examplary embodiment of the invention semidiagrammatically illustrated in the accompanying drawings and described in detail hereinafter.

DESCRIPTION OF EXEMPLARY EMBODIMENT OF INVENTION

Figure 1:
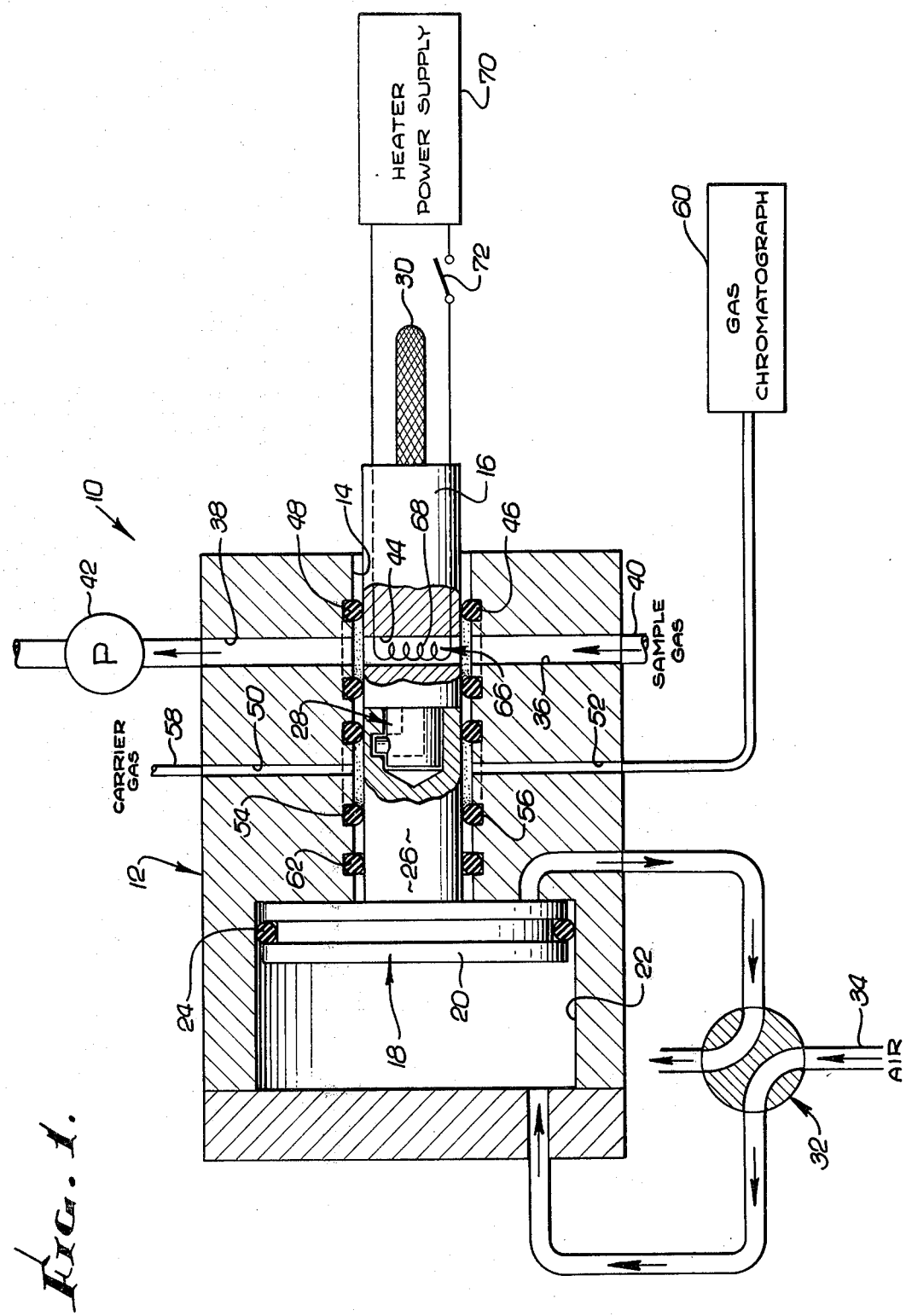
FIG. 1 is a semidiagrammatic longitudinal sectional view showing a concentration valve of the invention in a sampling position.

Referring to the drawings, the concentration valve of the invention is designated generally therein by the numeral 10 and comprises a housing 12 provided with a cylinder 14 for a cylindrical plug or cartridge 16. Connected to the cylindrical plug 16 is a pneumatic actuating means 18 for longitudinally moving the cylindrical plug between a sampling position, FIG. 1, and an analyzing position, FIG. 2, the significance of which positions will be discussed in more detail hereinafter.

More particularly, the actuating means 18 comprises a piston 20 reciprocable in a cylinder 22 coaxial with the cylinder 14, the piston 20 being sealed with respect to the cylinder 22 by an O-ring 24. The piston 20 is provided with an axial stem 26 which projects into the cylinder 14 and to which the cylindrical plug or cartridge 16 is secured by a readily releasable connecting means 28. The latter may be of any suitable construction, and is shown as a bayonet connection for purposes of illustration. The outer end of the cylindrical cartridge 16 is provided with a handle 30 for use in connecting the cartridge to and/or disconnecting it from the stem 26 of the piston 20.

Figure 2:
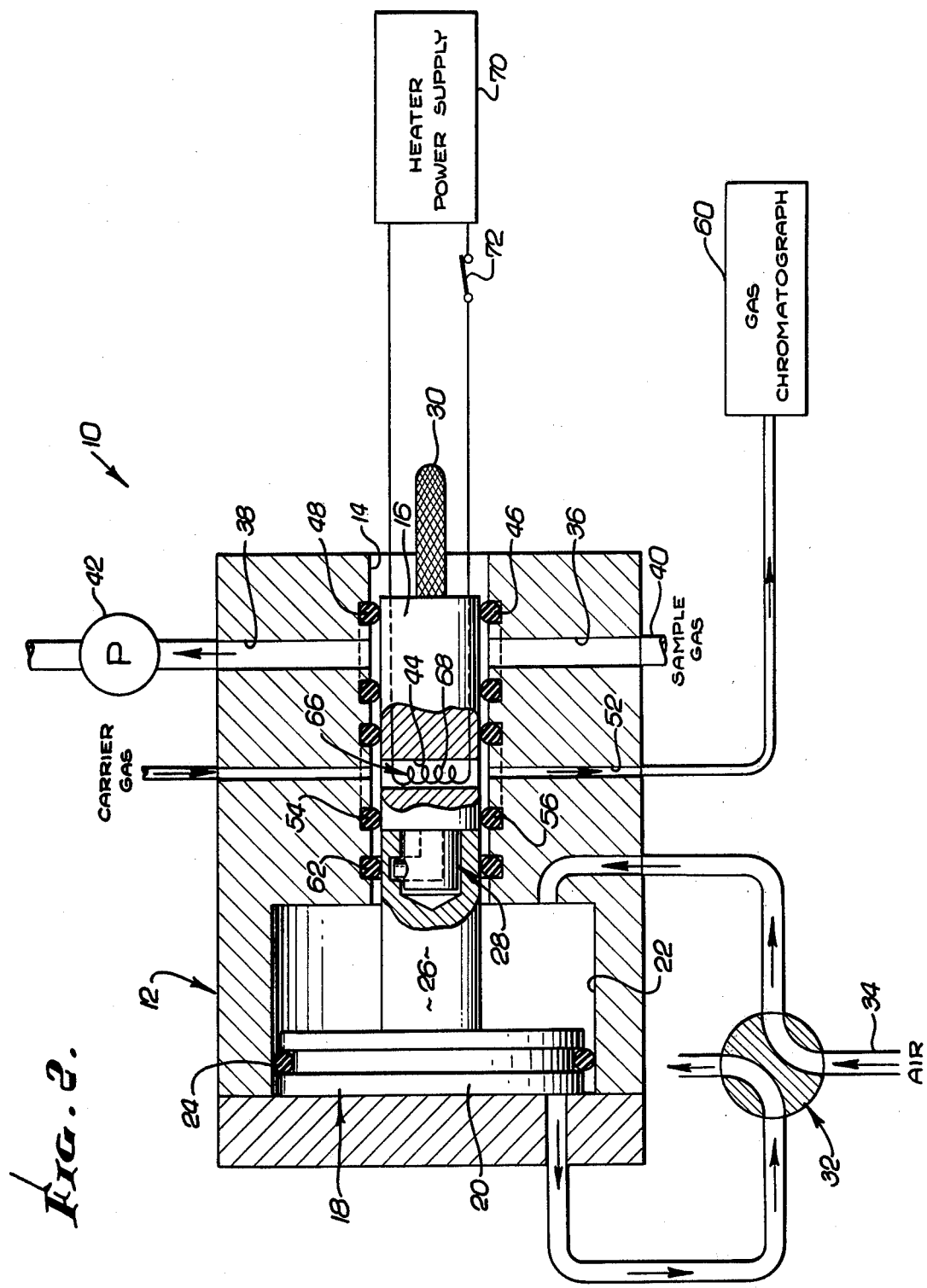
FIG. 2 is a view similar to FIG. 1, but showing the concentration valve in its analyzing position.

A selector valve means 32 selectively directs air under pressure from a source 34 to either the outer end of the piston 20, FIG. 1, or the inner end thereof, FIG. 2, to displace the cylindrical cartridge 16 longitudinally to its sampling position, FIG. 1, or its analyzing position, FIG. 2. Thus, the actuating means 18 displaces the cylindrical cartridge 16 betwwen its sampling and analyzing positions quickly and positively.

The cylinder 14 for the cartridge 16 is provided with circumferentially spaced, diametrally opposed inlet and outlet ports 36 and 38 for a sample gas, such as air, from any desired source 40 known as or suspected of containing a gaseous material or materials detection of which is desired. Connected to the outlet port 38 is a suction pump 42. In the sampling position, a diametral passage 44 through the cylindrical cartridge 16 registers with the inlet and outlet ports 36 and 38 so that the pump 42 draws the sample gas from the source 40 through the passage 44. O-rings 46 and 48 encircling the ports 36 and 38 seal the ends of the diametral passage 44 with respect to the ports 36 and 38.

In the analyzing position of the cylindrical cartridge 16, as shown in FIG. 2, the diametral passage 44 registers with carrier-gas inlet and outlet ports 50 and 52 the ends of which are sealed relative to the ends of the diametral passage 44 by O-rings 54 and 56. The inlet port 50 communicates with a suitable source 58 of the desired carrier gas, which may be helium, for example, while the outlet port 52 leads to a gas chromatograph 60, or other suitable analyzing apparatus.

It will be noted that the cylindrical cartridge 16 and the piston stem 26 are of the same diameter and that the various seals 46, 48, 54 and 56 engage the cartridge 16 and/or the stem 26, depending upon whether the cartridge is in its sampling or analyzing positions. The inner end of the cylinder 22 for the piston 20 is isolated by an O-ring 62 encircling the piston stem 26.

Disposed in the diametral passage 44 through the cylindrical cartridge 16 is an adsorbing means 66 capable of adsorbing the gaseous material or materials to be detected, as the sample gas flows through the diametral passage 44 in the sampling position of the cartridge. After the sample gas has been caused to flow over the adsorbing means 66 for the desired length of time, the pneumatic means 18 is actuated to shift the cylindrical cartridge 16 to its analyzing position, shown in FIG. 2 of the drawings. The adsorbed gaseous vapor or vapors are desorbed by heating and are delivered by the carrier gas to the gas chromatograph 60 for analysis. In this connection, the adsorbing means 66 may consist of or comprise an electrical resistance heating element 68 suitably connected to a heater power supply 70 through a switch 72, the latter being closed, as shown in FIG. 2, during desorbing.

It is thought that the operation of the concentration valve 10 will be clear from the foregoing so that only a short summary is necessary at this stage. Briefly, with the cylindrical cartridge in its sampling position, FIG. 1, the suction pump 42 is operated to draw the sample gas past the adsorbing means 66, which adsorbs the gaseous vapor or vapors to be detected. After a predetermined adsorbing time, the pump 42 is shut off and the selector valve means 32 is energized in a direction to shift the cylindrical cartridge 16 to its analyzing position, FIG. 2. The switch 72 is closed to energize the heating element 68, which desorbs the adsorbed gaseous material or materials. These are picked up by the carrier gas from the source 58 and are delivered to the gas chromatograph 60 for analysis. The cartridge 16 may be changed readily to detect a different gaseous material or materials.

Although an examplary embodiment of the invention has been disclosed for illustrative purposes, it will be understood that various changes, modifications and substitutions may be incorporated in such embodiment without departing from the invention as hereinafter claimed.

I claim as my invention:

1. In a concentration valve for a gas detecting apparatus, or the like, the combination of:
   (a) a cylinder having circumferentially spaced, diametrically opposed inlet and outlet ports for a sample gas, and having circumferentially spaced, diametrically opposed inlet and outlet ports for a carrier gas longitudinally spaced from and in the same longitudinal plane as the sample-gas inlet and outlet ports;
   (b) a cylindrical plug provided with a diametrical passage therethrough having ends respectively adapted to communicate with said sample-gas inlet and outlet ports, or with the carrier-gas inlet and outlet ports, said cylindrical plug being movable longitudinally of said cylinder between a sampling position wherein said passage therethrough communicates with said sample-gas inlet and outlet ports and an analyzing position wherein said passage therethrough communicates with said carrier-gas inlet and outlet ports;
   (c) adsorbing means in said passage through said cylindrical plug and operable to adsorb in said sampling position;
   (d) means for heating said adsorbing means in said analyzing position;
   (e) actuating means for longitudinally moving said cylindrical plug between said sampling and analyzing positions, said actuating means comprising a second cylinder coaxial with the cylinder first mentioned, a piston in said second cylinder, means for securing said cylindrical plug to said piston, and valve means for selectively directing air under pressure to opposite ends of said piston; and
   (f) said means for securing said cylindrical plug to said piston comprising a readily releasable connecting means.

2. In a concentration valve for a gas detecting apparatus, or the like, the combination of:
   (a) a cylindrical plug provided with a diametral passage therethrough having ends respectively adapted to communicate with sample-gas inlet and outlet ports, or with carrier-gas inlet and outlet ports spaced longitudinally from and in the same longitudinal plane as the sample-gas inlet and outlet ports;
   (b) adsorbing means in said diametral passage through said cylindrical plug and operable to adsorb when the ends of said diametral passage communicate with the sample-gas inlet and outlet ports; and
   (c) readily releasable connecting means for securing said cylindrical plug to means for reciprocating said cylindrical plug between a position where the ends of said diametral passage communicate with the sample-gas inlet and outlet ports and a position wherein the ends of said dimetral passage communicate with the carrier-gas inlet and outlet ports.

3. In a concentration valve for a gas detecting apparatus, or the like, the combination of:
   (a) a cylinder having circumferentially spaced, diametrically opposed inlet and outlet ports for a sample gas, and having circumferentially spaced, diametrically opposed inlet and outlet ports for a carrier gas longitudinally spaced from and in the same longitudinal plane as the sample-gas inlet and outlet ports;
   (b) a second cylinder coaxial with the cylinder first mentioned;
   (c) a piston in said second cylinder;
   (d) an axial stem on said piston and disposed in said first-mentioned cylinder;
   (e) valve means for selectively directing air under pressure to opposite ends of said piston; and
   (f) readily releasable connecting means for securing to said axial stem a cylindrical plug reciprocable in said first-mentioned cylinder and provided with a diametral passage therethrough having ends respectively adapted to communicate with the sample-gas inlet and outlet ports, or with the carrier-gas inlet and outlet ports.

* * * * *